(12) United States Patent
Heywood et al.

(10) Patent No.: US 10,078,054 B2
(45) Date of Patent: Sep. 18, 2018

(54) SYSTEMS AND METHODS FOR DETECTING NITRIC OXIDE

(71) Applicant: AOBIOME LLC, Cambridge, MA (US)

(72) Inventors: James Heywood, Newton, MA (US); David R. Whitlock, Cambridge, MA (US)

(73) Assignee: AOBIOME LLC, Cambridge, MA (US)

( * ) Notice: Subject to any disclaimer, the term of this patent is extended or adjusted under 35 U.S.C. 154(b) by 0 days.

(21) Appl. No.: 15/309,563

(22) PCT Filed: May 7, 2015

(86) PCT No.: PCT/US2015/029654
§ 371 (c)(1),
(2) Date: Nov. 8, 2016

(87) PCT Pub. No.: WO2015/171872
PCT Pub. Date: Nov. 12, 2015

(65) Prior Publication Data
US 2017/0184507 A1   Jun. 29, 2017

Related U.S. Application Data

(60) Provisional application No. 61/990,250, filed on May 8, 2014.

(51) Int. Cl.
*G01N 21/78* (2006.01)
*G01N 31/22* (2006.01)
(Continued)

(52) U.S. Cl.
CPC ............ *G01N 21/78* (2013.01); *G01N 21/783* (2013.01); *G01N 21/84* (2013.01); *G01N 31/22* (2013.01); *G01N 31/227* (2013.01); *G01N 21/293* (2013.01); *G01N 25/00* (2013.01); *G01N 33/0057* (2013.01); *G01N 33/22* (2013.01); *G01N 33/227* (2013.01); *G01N 2001/022* (2013.01); *G01N 2001/028* (2013.01); *G01N 2021/7759* (2013.01); *H05K 999/99* (2013.01)

(58) Field of Classification Search
CPC ...... G01N 21/78; G01N 31/22; G01N 33/227; G01N 33/22; G01N 2021/7759; G01N 31/227; G01N 33/0057; G01N 2001/022; G01N 2001/028; G01N 21/293; G01N 21/783; G01N 21/84; G01N 25/00
See application file for complete search history.

(56) References Cited

U.S. PATENT DOCUMENTS 5,912,115 A * 6/1999 Hyman .................... C12Q 1/04
422/50
7,897,399 B2   3/2011 Hyde et al.
(Continued)

*Primary Examiner* — Jennifer Wecker
(74) *Attorney, Agent, or Firm* — Lando & Anastasi, LLP

(57) ABSTRACT

A system and method is provided for detection at least one of nitrite (NO2), nitric oxide (NO), nitrogen dioxide (NO2), and other nitrogen oxides ($NO_x$) on a substrate, such as skin. According to one aspect, a diagnostic device for measuring a concentration of at least one of nitrite (NO2), nitrogen dioxide (NO2), nitric oxide (NO), and other nitrogen oxides ($NO_x$) on a substrate comprises a patch comprising at least one chemical compound capable of reacting with the at least one of nitrite, nitrogen dioxide, nitric oxide, and other nitrogen oxides to provide an indicator.

28 Claims, 1 Drawing Sheet

(51) Int. Cl.
*G01N 21/84* (2006.01)
*G01N 21/29* (2006.01)
*G01N 33/22* (2006.01)
*G01N 25/00* (2006.01)
*G01N 1/02* (2006.01)
*G01N 21/77* (2006.01)
*G01N 33/00* (2006.01)

(56) References Cited

U.S. PATENT DOCUMENTS

| | | |
|---|---|---|
| 8,003,399 B2 | 8/2011 | Song et al. |
| 2004/0078219 A1 | 4/2004 | Kaylor et al. |
| 2007/0048182 A1* | 3/2007 | Song .................... G01N 33/526 422/400 |
| 2009/0029480 A1* | 1/2009 | Loane .................... G01N 21/78 436/170 |
| 2012/0003746 A1* | 1/2012 | Amisar .................. G01N 31/22 436/110 |
| 2012/0107949 A1* | 5/2012 | Haas ...................... G01N 21/78 436/164 |
| 2012/0321724 A1 | 12/2012 | Bryan |
| 2014/0039280 A1* | 2/2014 | Allen .................... A61B 5/412 600/309 |
| 2014/0113383 A1 | 4/2014 | Jorgensen et al. |
| 2015/0160245 A1* | 6/2015 | Lieberman ........... G01N 33/523 506/12 |
| 2015/0316483 A1* | 11/2015 | Deans .................... G01N 21/76 506/12 |

* cited by examiner

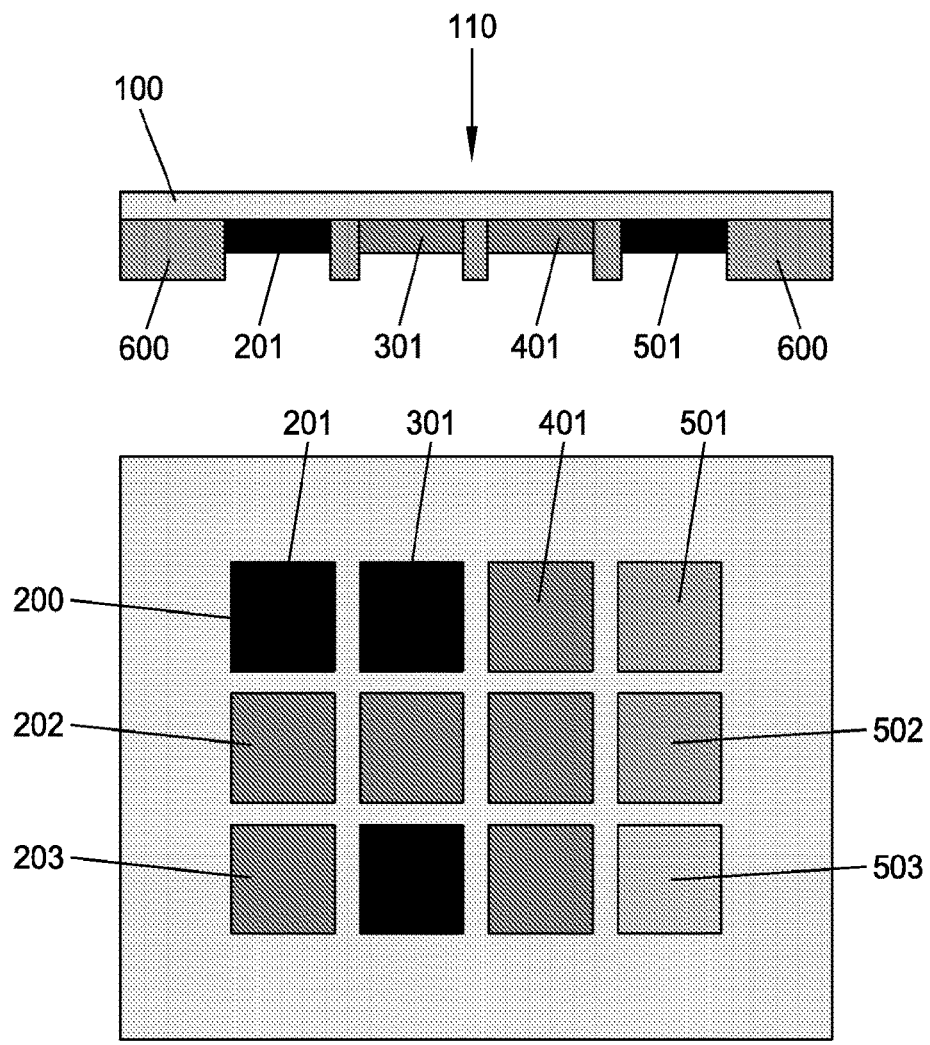

SYSTEMS AND METHODS FOR DETECTING NITRIC OXIDE

CROSS-REFERENCE TO RELATED APPLICATIONS

This application is a U.S. national phase application, and claims the benefit of priority under 35 U.S.C. § 371, of International (PCT) Patent Application Ser. No. PCT/US2015/029654, titled SYSTEMS AND METHODS FOR DETECTING NITRIC OXIDE and filed on May 7, 2015, which in turn claims priority to U.S. Provisional Application No. 61/990,250, filed May 8, 2014, the contents of which are incorporated herein by reference in their entireties.

FIELD OF THE DISCLOSURE

A system and method is provided for detection at least one of nitrite ($NO_2^-$), nitric oxide (NO), nitrogen dioxide ($NO_2$), and other nitrogen oxides ($NO_x$) on a substrate, such as skin.

SUMMARY

According to one aspect, a diagnostic device for measuring a concentration of at least one of nitrite ($NO_2^-$), nitrogen dioxide ($NO_2$), nitric oxide (NO), and other nitrogen oxides ($NO_x$) on a substrate comprises a patch comprising at least one chemical compound capable of reacting with the at least one of nitrite, nitrogen dioxide, nitric oxide, and other nitrogen oxides to provide an indicator.

According to various embodiments, the diagnostic device can further comprise any one or a combination of the following: the substrate is a skin surface; the indicator is a color; the intensity of the color correlates to the concentration of at least one of nitrite ($NO_2^-$), nitrogen dioxide ($NO_2$), nitric oxide (NO), and other nitrogen oxides ($NO_x$); a recording device; the recording device is a camera, such as a digital camera; a component on a first surface of the patch for securing the device to the surface; the component comprises an adhesive; a transparent layer on a second side of the patch; the patch comprises at least one pad which comprises the chemical compound capable of reacting with the at least one of nitrite, nitrogen dioxide, nitric oxide, and other nitrogen oxides to provide an indicator; the chemical compound is an aromatic primary amine; at least one of nitrite, nitrogen dioxide, nitric oxide, and other nitrogen oxides reacts with the aromatic primary amine to provide a diazonium ion; and the patch further comprises a membrane to provide a detection zone, the membrane comprising a nucleophilic aromatic amine detection reagent capable of reacting with the diazonium ion to form an azo indicator to exhibit a color that is different from a color of the nucleopilic aromatic amine detection reagent.

According to another aspect, a method for measuring a concentration of at least one of nitrite ($NO_2^-$), nitrogen dioxide ($NO_2$), nitric oxide (NO), and other nitrogen oxides ($NO_x$) on a substrate comprises: securing to the substrate a patch comprising at least one chemical compound capable of reacting with the at least one of nitrite, nitrogen dioxide, nitric oxide, and other nitrogen oxides to provide an indicator; monitoring the indicator over a predetermined period of time to provide at least one measurement; and comparing the at least one measurement to a known value to provide the concentration of the at least one of nitrite ($NO_2^-$), nitrogen dioxide ($NO_2$), nitric oxide (NO), and other nitrogen oxides ($NO_x$).

According to various embodiments, the method can further comprise any one or a combination of the following: securing the substrate to a skin surface; recording the indicator with a recording device; recording the indicator with a camera, such as a digital camera; providing a color indicator; providing the indicator so that the intensity of the color correlates to the concentration of at least one of nitrite ($NO_2^-$), nitrogen dioxide ($NO_2$), nitric oxide (NO), and other nitrogen oxides ($NO_x$); providing the patch with a chemical compound capable of reacting with the at least one of nitrite, nitric oxide, and other nitrogen oxides to provide an indicator is an aromatic primary amine; providing the indicator as a diazonium ion; and providing the patch with a membrane to provide a detection zone, the membrane comprising a nucleophilic aromatic amine detection reagent capable of reacting with the diazonium ion to form an azo indicator to exhibit a color that is different from a color of the nucleopilic aromatic amine detection reagent.

According to one aspect, a test patch is provided for measuring the NO/NOx status of the skin over time by attaching a patch containing chemicals that change color on reaction with NO, $NO_2$ and nitrite and following the color change over time by periodically recording the colors of the patches with a digital camera, correlating those colors with known NO/NOx levels.

According to one aspect, a diagnostic test patch comprises a transparent film upon which a multiplicity of reagent pads on which an aromatic primary amine is disposed that is capable of reacting with a nitrite or nitrite derivative in the sample to form a diazonium ion; and a porous membrane defining a discrete detection zone that is separate and distinct from the reagent pad and within which is contained a nucleophilic aromatic amine detection reagent, the detection reagent being capable of reacting with the diazonium ion to form an azo indicator, the azo indicator exhibiting a color that is different than the color of the detection reagent.

Still other aspects, embodiments, features and advantages of these exemplary aspects and embodiments, are discussed in detail below. Any feature, advantage, implementation, embodiment, or example may be combined or form a part of any aspect or any embodiments in any manner consistent with at least one of the principles disclosed herein," and references to "an embodiment," "some embodiments," "an alternate embodiment," "various embodiments," "one embodiment," "example," "feature," "advantage," "implementation" or the like are not necessarily mutually exclusive and are intended to indicate that a particular feature, embodiment, structure, or characteristic described may be included in at least one aspect. The appearances of such terms herein are not necessarily all referring to the same embodiment.

DESCRIPTION OF THE FIGURES

Various aspects of at least one embodiment are discussed below with reference to the accompanying figures, which are not intended to be drawn to scale. The figures are included to provide illustration and a further understanding of the various aspects and embodiments, and are incorporated in and constitute a part of this specification, but are not intended as a definition of the limits of the invention. In the figures, each identical or nearly identical component that is illustrated in various figures is represented by a like numeral. For purposes of clarity, not every component may be labeled in every FIGURE. In the figures:

FIG. 1 presents a schematic of a diagnostic system, in accordance with certain aspects and embodiments of the disclosure.

DETAILED DESCRIPTION

Research showing the importance of nitric oxide (NO) in the physiology of subjects, such as humans and animals continues to accumulate. In physiology, NO is a signaling molecule. NO may be generated at a site, diffuse some distance, and activate a sensor. The sensor may sense the sum of NO from all sources including the background. The sensor may then trigger downstream pathways to effect the physiological changes that the NO signal is regulating. For example, vascular tone may be regulated by the level of NO present at the endothelium.

Nitrite ($NO_2^-$) is also an important signaling molecule which can act as a precursor of NO. The physiology of nitrite is less well understood, and there is substantial cross-talk between the NO and nitrite pathways.

The present disclosure provides for systems and methods for measuring at least one of NO, nitrite ($NO_2^-$), nitrogen dioxide ($NO_2$), and other nitrogen oxides ($NO_x$). In certain aspects and embodiments, a concentration of one or more of NO, nitrite ($NO_2^-$), nitrogen dioxide ($NO_2$), and other nitrogen oxides ($NO_x$) may be measured. The at least one of NO, nitrite ($NO_2^-$), nitrogen dioxide ($NO_2$), and other nitrogen oxides ($NO_x$) may be measured on a substrate. The substrate may be any surface such as, for example, the surface of skin. In certain aspects and embodiments, the at least one of NO, nitrite ($NO_2^-$), nitrogen dioxide ($NO_2$), and other nitrogen oxides ($NO_x$) may be measured once, or a plurality of times over a predetermined period of time or at various time intervals. The measurements may be taken at various locations. In certain aspects and embodiments, the measurements may be imaged by a detector; in certain aspect and embodiments, the color change may be imaged by a wavelength sensitive detector. In certain aspects and embodiments, a camera, such as a digital camera may be used to record the images.

In certain aspects and embodiments, measurement may be achieved by way of a chemical-based color change patch detector. In certain aspects and embodiments, the patch detector can be applied to the substrate surface to be monitored.

Detection of nitrite in urine is disclosed by Xuedong Song et al in U.S. Pat. No. 8,003,399, entitled Nitrite Detection Technique (hereafter "Song et al.), which is herein incorporated by reference. Song et al uses an aromatic primary amine that is capable of reacting with nitrite to form a diazonium ion and then with an aromatic amine to form an azo dye indicator, but is silent with respect to detection of nitric oxide from skin.

A chemical analysis test which detects the presence of nitrite compounds is known as the Griess Technique or test, and is known and commercially available from a variety of sources such as: Griess Reagent Kit for Nitrite Determination (G-7921), Molecular Probes, Inc. product information Revised: 9 Jul. 2003. With the Griess technique, Nitrite is detected and analyzed by formation of a red pink color upon treatment of a $NO_2^-$-containing sample with a Griess reagent. However, it is not known to use the Griess Technique or test to with respect to detection of nitric oxide from skin.

Detection of NO and nitrite in vivo in the mouth is disclosed by Bryan in US 20120321724 A1, entitled Method of Measuring and Monitoring In Vivo Nitrite Levels (hereinafter Bryan), which is herein incorporated by reference. However, Bryan relates only to NO and nitrite from saliva or breath and is silent with respect to detection of nitric oxide from skin.

Detection of NO in bodily fluids is disclosed by Ching-San Lai in U.S. Pat. No. 5,885,842, entitled Methods for the detection of nitric oxide in fluid media (hereinafter Ching-San Lai), which is herein incorporated by reference. However, Ching-San Lai is silent with respect to detection of nitric oxide from skin.

Detection of $NO_2$ in air with colorometric dosimiter badges is disclosed by Robert F. Rakowski et al. in U.S. Pat. No. 3,578,552, entitled Colorimetric Dosimeter for Nitrogen Dioxide (hereinafter Rakowski et al.), which is herein incorporated by reference. However, Rakowski et al detection and monitoring is limited to high concentrations of $NO_2$ for personnel safety and Rakowski et al. is silent with respect to detection of nitric oxide from skin.

Many different types of NO sensors are discussed by Roderick A. Hyde et al in U.S. Pat. No. 7,897,399, entitled Nitric Oxide Sensors and Systems (hereinafter Hyde et al), which is herein incorporated by reference. However, Hyde et al sensors are only used in conjunction with the monitoring and control of a photolabile NO source. It is silent with respect to measurement of both NO and nitrite and therefore with respect to detection of nitric oxide from skin.

FIG. 1 shows one aspect of a patch detector of the present disclosure. This embodiment comprises a sensor array patch 110 comprising twelve (12) chemical patches 502, 503 arranged in four columns 201, 301, 401, 501 of three rows 200, 202, 203. It is to be appreciated that any number of patches 502, 503, in any arrangement can be used according to embodiments of this aspect. As disclosed herein, the chemical patches 502, 503 can be configured to change color with contact with at least one of NO, nitrite ($NO_2^-$), nitrogen dioxide ($NO_2$), and other nitrogen oxides ($NO_x$). The chemical patches may have different chemicals and concentrations so that the development of color change over time is a function of NO/NOx flux from the skin. A pressure sensitive adhesive 600, according to some embodiments may be slightly thicker than the chemical patches so that when the adhesive is pressed against a substrate, such as the surface of the skin, the adhesive and chemical patches may form separate cells with little cross-talk or cross-contamination between them. The sensor array 110 can also comprise a transparent support 100 on the surface opposite the adhesive surface.

With this arrangement, measurement of at least one of NO, nitrite ($NO_2^-$), nitrogen dioxide ($NO_2$), and other nitrogen oxides ($NO_x$) are achieved by way of a chemical-based color change. In certain embodiment, the color change may be imaged by a color detector, for example, the color change may be imaged by a wavelength sensitive detector. For example, a camera, such as a digital camera may be used to record the images.

In certain aspects and embodiments of this disclosure, a patch (not illustrated) comprising a chemical mixture that changes color upon exposure to at least one of NO, nitrite, and other nitrogen oxides is provided. The patch may be in the form of a sensor. The change in color may be monitored over time, such as a predetermined period of time. A portable imaging device such as, for example, a cell phone camera may be used to record and/or monitor the change in color over time. Several readings of the changes in color may be taken over time; alternatively a single reading may be taken. Depending on the light source that is available, particular Griess reagents, including an aromatic primary amine that is capable of reacting with nitrite, NO, or other nitrogen oxides to form a diazonium ion and then with an aromatic amine to form an azo dye indicator may be chosen to optimize the signal to noise ratio. Reference color spots may be placed on the patch or the sensor so that the recording device, monitoring device or imaging device and its software can manipulate the image, perform ratio comparisons, and calibrate a sensor array.

In certain aspects and embodiments in which the sensor or the patch is placed on a skin surface of a subject, use of a hydrophilic membrane in the diagnostic device may be desirable. Nitrite is water soluble, thus, contact through a hydrophilic membrane that can allow sweat to wick into the Griess reagents is desirable. NO is a gas so using a hydrophobic porous membrane will block liquid flow but allow NO to diffuse and react.

In certain aspect and embodiments, the system may comprise a transparent outer layer that protects the chemical layers from ambient air and from being disturbed during measurements or recordings. The chemical layer may be divided into a multiplicity of independent cells (or pads), which may be isolated from the others by the pressure-sensitive adhesive that holds the assembly to the substrate, such as the surface of the skin, during the measurement or recording. The multiple cells may have different chemicals and concentrations so that the development of the color change over time is a function of NO/NOx flux from the skin. The system may have specific channels or openings between the mix of the independent cells (or pads) and the skin to provide additional control, i.e. by retarding or providing for the concentration of any of nitrite ($NO_2^-$), nitrogen dioxide ($NO_2$), nitric oxide (NO), and other nitrogen oxides ($NO_x$) to flow between the cells and the skin. These channels may be diffusive bathers which restrict the diffusion of gases, hydrophilic or hydrophobic barriers, ion exchange membranes which block anions or cations or other barriers with a degree of selection in permeability such as, for example, ion exchange membranes which selectively block anions or cations.

The time-course of the NO/NOx evolution may be monitored for example by taking time-stamped photos. The system may be packaged in a sealed pouch which is opened at time of use.

NO related species are known to react with other species to either generate or quench fluorescence, and in certain aspects and embodiments of this disclosure may be used as an alternative to chemicals that may provide a color. These fluorophores have been used by NO researchers to detect and quantify the presence of NO in various environments and tissues.

Compounds which form fluorescent and luminescent markers on reaction with NO are well known in the art, as for example in the review article: Yang Y, Zhao Q, Feng W, Li E Luminescent chemodosimeters for bioimaging. Chem Rev. 2013 Jan. 9;113(1):192-270. doi: 10.1021/cr2004103. Epub 2012 Jun. 18 (hereinafter Zhao et al.), which is herein incorporated by reference. Zhao et al discuss multiple compounds including fluorophores coupled to a phenyldiamine which blocks the fluorescence, but upon reaction with NO, the phenyldiamine forms a triazole group which is less electron withdrawing, thereby blocking of fluorescence is abolished. Other fluorophores and luminophores for measuring NO may comprise:
1. Fluoresceine as Fluorophore
2. BODIPY (boron-dipyrromethene) as Fluorophore
3. Acridine and Anthraquinone As Fluorophores
4. Tricarbocyanine Dye As Fluorophore
5. Phosphorescent Heavy-Metal Complex As Luminophore
6. NO-Induced Diazo-Ring-Generation Process
7. NO-Induced Spirolactam-Ring-Opening Process
8. NO-Triggered Selective Ligand Dissociation of Metal Complex, and
9. NO-Triggered Reduction of Cu2+ and Release of Fluorescent Ligand.

According to aspects and embodiments disclosed herein, these and other fluorophore and luminophore generating schemes may be used. They may be used in ways that are very similar to how the system with Griess reagents is used. For example, they can be packaged in layers supported on a transparent membrane, such as polyethylene teraphthalate, which is substantially impervious to air, nitrite, NO and $NO_2$. During storage, materials with reduced permeability are desired. According to aspects and embodiments, aluminum coated polyester is acceptable.

According to aspects and embodiments, during storage before use, a release layer (not shown) may be placed against the pressure sensitive adhesive to both protect the chemical patches from ambient air and prevent the pressure sensitive adhesive from sticking in undesirable ways.

Having described above several aspects of at least one embodiment, it is to be appreciated various alterations, modifications, and improvements will readily occur to those skilled in the art. Such alterations, modifications, and improvements are intended to be part of this disclosure and are intended to be within the scope of the invention. Accordingly, the foregoing description and drawings are by way of example only.

The invention claimed is:

1. A diagnostic device for measuring a concentration of at least one of nitrite ($NO_2^-$), nitrogen dioxide ($NO_2$), nitric oxide (NO), and other nitrogen oxides ($NO_x$) on a skin surface, the diagnostic device comprising:
   a patch comprising:
      at least one chemical compound capable of reacting with the at least one of nitrite, nitric oxide, nitrogen dioxide and other nitrogen oxides to provide an indicator,
      a hydrophobic microporous membrane on a first surface of the patch configured to block liquid flow and capable of allowing gas to diffuse and react with the at least one chemical compound, and
      a component comprising an adhesive adjacent to the hydrophobic microporous membrane on the first surface of the patch for securing the device to the skin surface.

2. The diagnostic device of claim 1, wherein the indicator is a color.

3. The diagnostic device of claim 2, wherein the intensity of the color correlates to the concentration of at least one of nitrite ($NO_2^-$), nitrogen dioxide ($NO_2$), nitric oxide (NO), and other nitrogen oxides ($NO_x$).

4. The diagnostic device of claim 1, further comprising a recording device.

5. The diagnostic device of claim 4, wherein the recording device is a camera, such as a digital camera.

6. The diagnostic device of claim 1, further comprising a transparent layer on a second surface of the patch.

7. The diagnostic device of claim 1, wherein the patch comprises at least one pad which comprises the chemical compound capable of reacting with the at least one of nitrite, nitrogen dioxide, nitric oxide, and other nitrogen oxides to provide an indicator.

8. The diagnostic device of claim 7, wherein the chemical compound is an aromatic primary amine.

9. The diagnostic device of claim 8, wherein the at least one of nitrite, nitrogen dioxide, nitric oxide, and other nitrogen oxides reacts with the aromatic primary amine to provide a diazonium ion.

10. The diagnostic device of claim 9, wherein the device is configured to provide a detection zone, the detection zone comprising a nucleophilic aromatic amine detection reagent capable of reacting with the diazonium ion to form an azo indicator to exhibit a color that is different from a color of the nucleophilic aromatic amine detection reagent.

11. The diagnostic device of claim 7, further comprising at least one channel or barrier from the at least one pad to the skin surface to provide selective control of the concentration of any of nitrite ($NO_2^-$), nitrogen dioxide ($NO_2$), nitric oxide (NO), and other nitrogen oxides (NOx).

12. A method for measuring a concentration of at least one of nitrite ($NO_2^-$), nitrogen dioxide ($NO_2$), nitric oxide (NO), and other nitrogen oxides ($NO_x$) on a skin surface, the method comprising steps of:
securing to the skin surface a patch comprising at least one chemical compound to react with the at least one of nitrite, nitrogen dioxide, nitric oxide, and other nitrogen oxides and provide an indicator and a hydrophobic microporous membrane configured to block liquid flow and allow gas to diffuse and react with the at least one chemical compound, the patch being secured such that the hydrophobic microporous membrane faces the skin surface;
periodically monitoring the indicator over a predetermined period of time while the patch is secured to the skin surface to provide at least one measurement; and
comparing the at least one measurement to a known value to provide the concentration of the at least one of nitrite ($NO_2^-$), nitrogen dioxide ($NO_2$), nitric oxide (NO), and other nitrogen oxides ($NO_x$).

13. The method of claim 12, further comprising recording the indicator with a recording device.

14. The method of claim 13, wherein recording the indicator with a recording device comprises recording the indicator with a camera, such as a digital camera.

15. The method of claim 12, further comprising recording a time-course evolution of any of nitrite ($NO_2^-$), nitrogen dioxide ($NO_2$), nitric oxide (NO), and other nitrogen oxides ($NO_x$) by taking time-stamped photos.

16. The method of claim 12, wherein providing the indicator comprises providing a color indicator.

17. The method of claim 16, further comprising providing the indicator so that the intensity of the color correlates to the concentration of at least one of nitrite ($NO_2^-$), nitrogen dioxide, ($NO_2$), nitric oxide (NO), and other nitrogen oxides ($NO_x$).

18. The method of claim 12, further comprising providing the patch with at least one pad which comprises the chemical compound capable of reacting with the at least one of nitrite, nitrogen dioxide, nitric oxide, and other nitrogen oxides to provide an indicator, wherein the chemical compound is an aromatic primary amine.

19. The method of claim 18, wherein the indicator is diazonium ion.

20. The method of claim 19, further comprising providing the patch with a detection zone, the detection zone comprising a nucleophilic aromatic amine detection reagent capable of reacting with the diazonium ion to form an azo indicator to exhibit a color that is different from a color of the nucleophilic aromatic amine detection reagent.

21. The diagnostic device of claim 7, comprising an array of pads.

22. The diagnostic device of claim 21, wherein each pad of the array of pads comprises a different chemical compound or a different concentration of the chemical compound.

23. The diagnostic device of claim 22, further comprising a hydrophilic microporous membrane on the first surface of the patch capable of allowing sweat to absorb and react with the at least one chemical compound.

24. The diagnostic device of claim 7, wherein the chemical compound is a fluorophore or luminophore and the at least one of nitrite, nitrogen dioxide, nitric oxide, and other nitrogen oxides reacts with the fluorophore or luminophore to generate or quench fluorescence or luminescence.

25. The diagnostic device of claim 1, wherein the patch comprises a chemical mixture which changes color upon exposure to the at least one of nitrite, nitric oxide, nitrogen dioxide and other nitrogen oxides.

26. The method of claim 12, further comprising providing the patch with an array of pads, wherein each pad of the array of pads is provided with a different chemical compound or a different concentration of the chemical compound.

27. The method of claim 26, further comprising providing the patch with a hydrophilic microporous membrane capable of allowing sweat to absorb and react with the at least one chemical compound.

28. The method of claim 26, further comprising selectively retarding with a channel or barrier the diffusion of at least one of nitrite, nitrogen dioxide, nitric oxide or nitrogen oxides so different pads exhibit differential color development.

* * * * *